US008536216B2

(12) United States Patent
Dioguardi

(10) Patent No.: US 8,536,216 B2
(45) Date of Patent: Sep. 17, 2013

(54) COMPOSITIONS BASED ON AMINOACIDS

(75) Inventor: Francesco Saverio Dioguardi, Milan (IT)

(73) Assignee: Professional Dietetics S.R.L., Castel San Giovanni (PC) (IT)

( * ) Notice: Subject to any disclaimer, the term of this patent is extended or adjusted under 35 U.S.C. 154(b) by 188 days.

(21) Appl. No.: 13/014,294

(22) Filed: Jan. 26, 2011

(65) Prior Publication Data
US 2011/0124697 A1 May 26, 2011

Related U.S. Application Data

(62) Division of application No. 10/332,236, filed as application No. PCT/IB01/01181 on Jun. 28, 2001, now Pat. No. 7,902,250.

(30) Foreign Application Priority Data

Jul. 4, 2000 (IT) .............................. TO2000A0674

(51) Int. Cl.
*A61K 31/40* (2006.01)
*A61K 31/195* (2006.01)

(52) U.S. Cl.
USPC ........................... 514/419; 514/561; 514/562

(58) Field of Classification Search
USPC ........................ 514/419, 561, 562
See application file for complete search history.

(56) References Cited

U.S. PATENT DOCUMENTS

| | | | |
|---|---|---|---|
| 4,059,694 A | 11/1977 | Norton et al. | |
| 5,032,608 A | 7/1991 | Dudrick | |
| 5,036,052 A * | 7/1991 | Ozeki et al. | 514/5.5 |
| 5,198,465 A | 3/1993 | Dioguardi | |
| 5,276,018 A | 1/1994 | Wilmore | |
| 6,218,420 B1 * | 4/2001 | Dioguardi | 514/419 |
| 6,270,750 B1 | 8/2001 | Dioguardi | |
| 6,329,342 B1 | 12/2001 | Kauffman et al. | |

FOREIGN PATENT DOCUMENTS

| | | |
|---|---|---|
| EP | 0483614 A1 | 5/1992 |
| WO | 9826774 A | 6/1998 |

OTHER PUBLICATIONS

Wright, "Amino acids in the Treatment of Ischaemic Heart Disease", Journal of Molecular and Cellular Cardiology, 17(5), pp. 441-443 (1985).
C.E. Heyliger et al., "Effects of Choline and Methionine Treatment on Cardiac Dysfunction of Diabetic Rats", Diabetes, 35(10), pp. 1152-1157 (1986).
M.B. Peterson et al..: "Free Amino-Acids in Congestive Heart Failure" Journal of Molecular and Cellular Cardiology, vol. 5, No. 2, 1973, pp. 139-147, XP001038535, ISSN: 0022-2828.
M.B. Peterson et al.: "Protein and Free Amino-Acid Metabolism in the Failing Canine Heart", Dhalla N.S. (Ed) Recent Advances in Studies on Cardiac Structure and, vol. 1973, No. RECD 1974, pp. 615-623, XP001037339, University Park Press,: Baltimore, MD, U.S.A.,: London, England Recd 1974), see p. 618-619: Protein synthesis.

* cited by examiner

*Primary Examiner* — Kevin E Weddington
(74) *Attorney, Agent, or Firm* — Sughrue Mion, PLLC

(57) ABSTRACT

Compositions based on amino acids are described, in particular for oral or parenteral use, suitable for treating heart insufficiency. The compositions according to the invention comprise up to 75% of the branched chain amino acids leucine, isoleucine and valine, as active ingredients. Preferably, the compositions also comprise, as further active ingredients, up to 50% of threonine and lysine. Other essential amino acids are preferably also provided (in particular methionine, phenylalanine, histidine, triphtophan) as well as non essential amino acids (in particular tyrosine and/or cyst(e)ine—i.e., cystine and cyst(e)ine). Other amino acids can be added, provided that their sum is in a percentage being lower than 20% with respect to the other active ingredients, and less than 10% for each single amino acid.

1 Claim, No Drawings

COMPOSITIONS BASED ON AMINOACIDS

This is a Divisional of application Ser. No. 10/332,236 filed Jan. 6, 2003, which is a 371 of PCT/IB01/01181 filed Jun. 28, 2001, which claims priority from TO 2000A000674 filed on Jul. 4, 2000; the contents of all of which are incorporated herein by reference in their entirety.

BACKGROUND OF THE INVENTION

The present invention refers to compositions based on amino acids, in particular for oral or parenteral use, suitable for the treatment of the heart insufficiency. National statistics indicate that, in the USA, chronic heart failure (CHF) incidence and prevalence have increased over the last twenty years, despite the increased resources devoted to its prevention (Sytkowski P. A. et al.; New England Journal of Medicine, 1990; 322: 1635-1641), and the significant progresses in availability of treatment of this particular disease (Pitt B. et al.; New England Journal of Medicine, 1999; 341: 709-717).

Chronic heart failure is no longer strictly deemed as the consequence of hypertension or valvular heart disease, but rather of coronary heart disease, and therefore of arteriosclerosis (Gheorghiade M. and Bonow R. O.; Circulation, 1998; 97: 282-289).

In all the patients suffering this disease, intolerance to physical exercise is one of the major clinical feature, which is consistent with the proceeding of the same pathology; in addition, a noticeable skeletal muscle atrophy, often in the absence of signs of severe malnutrition, is a quite constant accompanying feature of chronic heart failure of any grade (Mancini D. M. et al.; Circulation, 1992, 85: 1364-1373).

Mechanisms of muscle wasting have been recently reviewed in literature (Mitch W. E. and Goldberg A. L.; New England Journal of Medicine, 1996; 355: 1897-1905.

It has not yet been clarified whether metabolic abnormalities observed during local physical exercise are functionally associated with alterations detected in the systemic exercise (Okita K. et al.; Circulation, 1998; 98: 1886-1891), although a recent study concluded that, most probably, intrinsic differences in skeletal muscle metabolism, rather than vasodilatory dynamics, must be taken into account for explaining the increased metabolic responses of glycolitic type in moderate physical strain of CHF patients.

On the contrary, in strenuously exercising skeletal muscles, the enhanced vasoconstriction following inability to increase the vascular conductance, is the main reason of exertional fatigue, despite normal pressor response (Shoemaker J. K.; Circulation, 1999; 99: 3002-3008).

There is no therapeutic approach based on the clinical evidences described above.

Till now, in fact, the only therapeutic intervention that has proved unequivocally to be beneficial in improving symptoms and prolonging life in patients with chronic heart failure was is that one with ACE inhibitors (Bart B. A. et al.; Journal of the American College of Cardiology, 1997; 30: 1002-1008, e Gheorghiade M. and Bonow R. O.; Circulation, 1998; 97: 282-289), further improved by the more extensive beta receptor blockade given by spironolactones, as recently published (Pitt B. et al.; New England Journal of Medicine, 1999; 341: 709-717). Both drugs are mainly anti-hypertensive agents.

SUMMARY OF THE INVENTION

The present invention has the aim of indicating an absolutely innovative therapeutic approach to the problem of heart insufficiency.

A further aim of the invention is that of indicating compositions which are capable of determining a clean improvement of the muscle performance, particularly but not exclusively in patients suffering heart insufficiency.

Within this frame, the inventor has arrived to the formulation of compositions based on amino acids, as per the enclosed claims which are an integral part of the present description, which prove to be particularly effective for the proposed purposes.

Said compositions, being in particular provided for oral or parenteral use, are characterized by comprising, as main active ingredients, the branched chain amino acids leucine, isoleucine and valine, up to 75% of all the amino acids or active ingredients being present, by expressing the value in molecular weights. Preferably, the compositions according to the invention also comprise, as further active ingredients, threonine and lysine, where in particular threonine plus lysine are present up to 50% of all the amino acids or active ingredients being present, by expressing the value in molecular weights.

In case, the compositions can provide, as further active ingredients, other essential amino acids, in particular methionine and/or phenylalanine and/or histidine and/or triptophan, and non essential amino acids, in particular tyrosine and/or cyst(e)ine (i.e. cystine and cysteine).

Preferably, the sum of the amounts being expressed in molecular weights of threonine and lysine is greater than the sum of the single amounts of the other essential amino acids being provided, but in any case lower than the sum of the single amounts of the branched chain amino acids being provided. In addition, the amounts being expressed in molecular weight of threonine and of lysine can be each greater than the single amounts of the other essential amino acids being provided, but in any case lower than the single quantities of the branched chain amino acids being provided.

The compositions according to the invention can also comprise one or more further amino acids, with respect to those as previously indicated, the sum of which, expressed in molecular weight, is preferably lower than 20% with respect to the active ingredients, and less than 10% for each single further amino acid.

It should be noticed that, in general terms, a mixture of amino acids particularly suitable for nutritional use in humans should satisfy different requirements:
- the content of essential amino acids in the mixture should be in an adequate ratio to fulfill real human nutritional needs (and this can be optimized by the co-operative adjunction of adequate and small ratios of some non essential amino acids);
- the pH of the solution of the mixture should be substantially neutral, in order to prevent urinary calcium losses;
- the mixture should be safe, in respect to calcium balance (i.e.: with no urinary losses) and homocyst(e)ine production (i.e., preferably related to the amount of all amino acids, a strictly correct ratio of sulphur containing amino acids, with a ratio cyst(e)ine/methionine of at least 2:1 on a stoichiometric basis).

Within this frame, a possible formulation of the composition according to the invention, comprising essential amino acids (leucine, isoleucine, valine, threonine, lysine, methionine, phenylalanine, histidine, triptophan) and some non essential amino acids (tyrosine and cyst(e)ine), in different but fixed and co-operative molar ratios among them, is the following one:
- branched chain amino acids leucine (40-60% in molecular weight), isoleucine (20-40% in molecular weight) and valine (20-40% in molecular weight), preferentially in a stoichiometric ratio 2:1:1 among them, covering from 30 to 60% of the weight of the whole mixture;

threonine plus lysine, preferably in a w/w molar ratio with the above said branched chain amino acids between 20 and 50%, but with a threonine to lysine ratio in which threonine is from 10 to 50% more represented than lysine;

the above said branched chain amino acids plus threonine and lysine, whose sum of the molecular weight is in a stoichiometric ratio of 50 to 70% of a mixture also comprising histidine and other amino acids, were histidine is present in molar ratio up to 50% of the following amino acids:

cyst(e)ine (i.e., cystine and cysteine) and methionine, up to 50% of histidine (the ratio between cyst(e)ine and methionine should be is preferably of 50 to 200% greater for cyst(e)ine on a w/w molar ratio), phenylalanine and tyrosine, in molar ratio up to 50% of histidine (in which tyrosine is preferably represented up to 50% of the molar weight of phenylalanine), triptophan, up to 10% of the weight of all the other amino acids, on a molar weight basis.

It has to be noticed that any other amino acid can be summed to the above formulation, without altering the expected effects, if their sum would be in a percentage lower than 20% with respect to the other active ingredients (less that 10% for each single amino acid).

It should also be noticed that a significant characteristic of the above said formulation is that of having a pH in water solution comprised between 6.5 and 8.5, and therefore suitable for a safe oral or parenteral use, in humans or animals, according to needs. This feature prevents the excessive calcium urinary losses induced by protein sources of amino acids.

The effects on energy balance of the an amino acids mixture according to the invention as above indicated were the subject of a comparative study with creatine, on a weight ratio (w/w), or with no treatment, on a large group of volunteers submitted to a rigid protocol of alimentation and training.

Table 1 which follows shows the result of such a study, were the effect of the amino acids mixture according to the invention (24 g/d-1), creatine (25 g/d-1) and placebo have been compared to each other, after one month of and homogeneous treatment and training, in groups of athletes were:

Group 1 is the group treated with the mixture according to the invention;
Group 2 is the group treated with creatine;
Group 3 is the group treated with placebo.

TABLE 1

Bench press (Kg), Squat Romano (Kg) e maximal power productive performance on a braked bicycle ergometer (watt/kg max)

| Group | Bench press (Kg) | Squat Rom. (Kg) | Watt/Kg max |
|---|---|---|---|
| 1 | 180.7 ± 39.8 | 142.2 ± 35.5 | 10.2 ± 0.9 |
| 2 | 177 ± 34 | 148.5 ± 31.2 | 9.8 ± 0.6 |
| 3 | 173.2 ± 33.7 | 130.8 ± 33.5 | 8.2 ± 0.9 |

Different tests, as the one showed in Table 1, that either creatine and amino acids has a powerful effect. Both treated groups (i.e., Group 1 and Group 2) had significant improvements of performances over basal and no treatment group (Group 3).

In some athletes, also heart frequency rate and $VO_2$ max were registered while performing a treadmill test, before and at the end of this study.

The results for the group treated with the amino acids mixture according to the invention are strikingly different with respect to the no treatment group, and even if power obtained under effort by groups treated with amino acids and creatine was similar, the maximal values of heart frequency, $VO_2$ and power production peak was strikingly improved only in the amino acids treated group.

The following Tables 2 shows in particular the modifications induced by chronic administration of the amino acids mixture according to the invention in normal athletes (healthy).

TABLE 2

Cardiac frequency (FC), VO2 and peak power production (Watt), measured on a braked bicycle ergometer

| | FC max | $VO_2$ max | Watt max |
|---|---|---|---|
| Basal value | 185 ± 8.4 | 3.2 ± 0.4 | 227 ± 30 |
| Acute assumption | 191 ± 7.4 | 3.4 ± 0.2 | 241 ± 32 |
| Chronic assumption | 188 ± 8.6 | 3.9 ± 0.4 | 261 ± 29 |

This has led to study the effects of exercise in a pathogenically homogeneous population of chronic heart disease patients. As shown in Table 3 which follows, in said patients an elevate destruction of structural proteins is shown, as signaled by an increase in plasma concentrations of amino acids (Table 3 only shows amino acids of peculiar interest), is and this occurs after just 10 minutes of electrically braked bicycle ergometer, even at the very low maximal rate of energy produced by these patients.

TABLE 3

Cardiopathic patients under effort

| | Base | 60' |
|---|---|---|
| Leucine | 171 ± 19 | 184 ± 23 |
| Isoleucine | 84 ± 9 | 97 ± 14 |
| Valine | 197 ± 31 | 212 ± 28 |
| Lysine | 190 ± 19 | 263 ± 34 |
| Threonine | 158 ± 12 | 175 ± 21 |
| Phenylalanine | 72 ± 8 | 78 ± 8 |
| Tyrosine | 66 ± 7 | 73 ± 8 |
| Methionine | 27 ± 6 | 39 ± 9 |
| Cysteine | 3 ± 1 | 4 ± 3 |

Cardiac cachexia (the severe muscle wasting observed even in absence of malnutrition in chronic heart insufficiency patients), is a quite constant and noxious condition, clinically associated to chronic heart failure and potentially life threatening (Anker S. D. et al.; Lancet, 1997; 349:1050-1053).

To make understood the relevance of this evidence, in the following Table 4 plasma profiles are reported of amino acids as they can be detected in healthy athletes (weight lifters), that underwent to leg strenuous exercise (i.e., leading to exhaustion) for 45 minutes, after an overnight fasting.

TABLE 4

Athletes under effort

| | Base | 15' | 60' |
|---|---|---|---|
| Leucine | 111 ± 13 | 110 ± 9 | 122 ± 22 |
| Isoleucine | 56 ± 12 | 58 ± 14 | 59 ± 8 |
| Valine | 85 ± 20 | 84 ± 18 | 182 ± 19 |
| Lysine | 192 ± 24 | 201 ± 16 | 254 ± 18 |
| Threonine | 117 ± 11 | 98 ± 8 | 129 ± 11 |
| Phenylalanine | 71 ± 8 | 73 ± 9 | 79 ± 6 |

TABLE 4-continued

Athletes under effort

|  | Base | 15' | 60' |
|---|---|---|---|
| Tyrosine | 56 ± 9 | 58 ± 4 | 78 ± 8 |
| Methionine | 24 ± 4 | 26 ± 8 | 41 ± 3 |
| Cysteine | 0.3 ± 0.2 | 1 ± 0.6 | 3.2 ± 0.5 |

To reproduce plasma modifications being similar to the ones detected in chronic heart failure patients which cycle at 10 Watt for 10 minutes, these athletes should be obliged to at least 45 minutes of over-training exercise (the shown data have been in fact obtained by two training machines, Leg press and Leg extension, increasing loads to exhaustion).

In a subsequent study, the population of chronic heart disease patients has been submitted to acute and chronic tests, after a load of 10 g. of the amino acidic mixture according to the invention, and after one month of 5 g. of amino acids, t.i.d (15 g/d).

Maximum power in Watt (W max), time before exhaustion at W max in seconds (Time Before Exhaustion=TBE) and ventricular ejection fraction (VEF), registered by means of an electrically braked bicycle ergometer, after acute ingestion and after one month, are shown in Tables 5 and 6 which follow.

TABLE 5

Test on braked bicycle ergometer in chronic heart disease patients

| W max | TBE | VEF |
|---|---|---|
| 91.8 ± 8.4 | 10.5 ± 2.1 | 39.7 ± 7.6 |

Maximum power production (W max), time before exhaustion at W max in seconds (TBE), ventricular ejection fraction in % (VEF)

TABLE 6

Test on braked bicycle ergometer in chronic heart disease patients after treatment with the amino acids mixture according to the invention (4 weeks)

| W max | TBE | VEF |
|---|---|---|
| 103.9 ± 3.7 | 12.4 ± 2.6 | 43.4 ± 7.8 |

Maximum power production (W max), time before exhaustion at W max in seconds (TBE), ventricular ejection fraction in % (VEF)

No known drug can elicit similar results in CHD patients. On the other hand, these data are easily reproducible.

The efficiency of the mixture according to the invention can be explained from two viewpoints.

According to a first viewpoint, and as it can be noticed in the following Table 7, administration of the said mixture of amino acids according to the invention elicits an acute increased availability of glutamate in plasma.

TABLE 7

Amino acids plasma modifications induced by acute ingestion of the mixture according to the invention

|  | Base | 15' | 30' | 60' |
|---|---|---|---|---|
| Leucine | 55 ± 12 | 68 ± 16 | 109 ± 19 | 71 ± 9 |
| Isoleucine | 138 ± 21 | 156 ± 24 | 162 ± 31 | 147 ± 32 |
| Valine | 231 ± 18 | 256 ± 19 | 294 ± 32 | 249 ± 26 |
| Lysine | 173 ± 18 | 182 ± 17 | 194 ± 26 | 179 ± 18 |
| Threonine | 107 ± 14 | 121 ± 15 | 137 ± 21 | 120 ± 16 |
| Phenylalanine | 49 ± 7 | 56 ± 9 | 61 ± 10 | 55 ± 7 |

TABLE 7-continued

Amino acids plasma modifications induced by acute ingestion of the mixture according to the invention

|  | Base | 15' | 30' | 60' |
|---|---|---|---|---|
| Tyrosine | 55 ± 10 | 62 ± 9 | 65 ± 14 | 59 ± 7 |
| Methionine | 24 ± 4 | 30 ± 6 | 32 ± 9 | 27 ± 4 |
| Cysteine | 43 ± 5 | 54 ± 6 | 61 ± 8 | 49 ± 7 |
| Arginine | 75 ± 12 | 85 ± 15 | 97 ± 13 | 82 ± 16 |
| Glutamic acid | 32 ± 7 | 42 ± 6 | 44 ± 7 | 41 ± 5 |
| Glutamate | 479 ± 33 | 563 ± 69 | 606 ± 32 | 502 ± 43 |

This happens when citric acid cycle is fully active, and metabolic intermediates can be exported. Glutamate and the availability of the derived glutamic acid is correlated with nitric oxides (NOx) production. These molecules are involved in the control of vasodynamics, and their production is compromised in CHD patients, this leading to vasoconstriction in peripheral tissues, and thus to reduced $O_2$ extraction.

Normalization of NOx production, as predicted by increased glutamate-glutamine patterns, would therefore reduce peripheral vasoconstriction (i.e., ameliorate performances) and increase O2 extraction, as observed in the studies in connection with the invention.

According to a second viewpoint, fuel availability is the main control of the origin of energy from one or another substrate.

Availability of repeated bouts of amino acids, either glucogenic or chetogenic intermediates generating, has a sparing effect on glucose consumption for energetic purposes (as already shown, see Dioguardi F. S., Influence of the ingestion of branched chain amino acids on plasma concentrations of ammonia and free fatty acids, Journal of Strength and Conditioning Research 1997; 11(4): 242-245 -oral amino acids can also metabolically control triglycerides degradation and FFA (free fatty acids) appearance in plasma, thus available for cells). Experimental studies done in peripheral muscle and cardiac cells have shown that peculiar changes in enzyme activity can be detected in treated (with the amino acids mixture according to the invention) vs. untreated animals.

Thus, availability of peculiar ratios of branched chain amino acids, in particular when coupled to threonine and lysine (the former being the intramitochondrial precursor of succynilCoa, the latter promoting acylcarnitine syntheses, and FFA intramitochondrial transport) in the cited stoichiometric ratio, promotes oxidation of amino acids and FFA, either in muscle cells and also in cardiomyocites.

A peculiar role should be ascribed to threonine, whose transformation in succynilCoa, is as said, allows acetoacetate from ketogenic amino acids and from FFA to be splitted in two molecules of acetylCoa, contemporarily promoting oxaloacetate regeneration in the citric acid cycle for oxidation. This leads to abundance of either acetyl groups, or oxaloacetate-citrate, and NADH, from different origins, in mitochondrions.

Indeed, rising concentrations of acetylCoA are followed by activation of pyruvate carbossylase (PC), the enzyme promoting the reaction pyruvate+$CO_2$ oxaloacetate.

The sum of these events would promote abundant entry in citric acid cycle (the main energy producer of any body cell) of either acetyl groups and intermediates of the said cycle (mostly at committed steps as a-ketoglutarate and succinate), thus leading to abundance of oxaloacetate-citrate. The part of them not utilized for energy production is exported to cytoplasm as malonylCoA-malate or glutamic acid-glutamine, via mitochondria co-transporter systems.

In cytosol, this peculiar metabolic flow will inhibit pyruvate dehydrogenase, by 30 activation of pyruvate dehydrogenase kinase in presence of acetylcoA and NADH, avoiding pyruvate from lipid syntheses.

Experimentally, the presence of abundant NADH, ATP and citrate, in these conditions, down-regulates also phosphofructokinase, the rate limiting enzyme of glycolysis, avoiding pyruvate formation from glucose and diverting excess citrate to neoglucogenesis. This observation, if transported in the interpretation of what occurring in vivo in the volunteers, accounts for the rapid amelioration of resistance to fatigue either in athletes or in chronic heart failure disease patients.

In recent experimental studies (rats denervated of sciatic nerves), also some evidences are accumulating that, in muscles, LDH H isoenzymes sub-units are favorably is activated by the administration of the mixture according to the invention. This suggests that the eventual lactate production from pyruvate would be rapidly and more largely converted to pyruvate than in untreated animals. The result is that, in morphometric hystochemical evaluation of denervated muscles, metabolic dependence on glycolysis of energy production is reduced at least of 30%, as suggested by evaluation of ATPases concentrations in muscle cells.

Although said experimental data should cautiously transferred to a human physiological model, the clinical data are in agreement with the said observations. From the above description the feature of the present invention are clear, as well as its advantages.

From the above, it is in fact clear how the compositions according to the invention are particularly efficacious in the treatment of chronic heart insufficiency.

From the above, it is also clear that the compositions according to the invention are particularly efficacious also for improving muscle performance, particularly but not exclusively in chronic heart failure patients.

Within these frames, the compositions according to the invention are particularly efficacious:
- in all conditions of increased nitrogen needs, where no interference with calcium excretion is a relevant feature,
- in all conditions of normal nitrogen needs, where no interference with calcium excretion is a relevant feature, independently by any pathogenetic origin and therapeutic approach,
- in all conditions where an increased ventricular ejection fraction would be advantageous to the patients,
- in all conditions where an enhanced peripheral oxygen extraction would be advantageous to the patients,
- in all conditions where positive inotropism and/or anticatabolic effects should be improved in any striated muscles, metabolically enhancing contractility and/or improving peripheral oxygen extraction, where the compositions according to the invention are suitable for being added to and/or improving clinical effects of any other therapeutic schedule.

What is claimed is:

1. A composition consisting of leucine, isoleucine, valine, lysine, threonine, methionine, phenylalanine, tyrosine, cyst(e)ine, histidine, and tryptophan,
    wherein leucine, isoleucine and valine are present in the following molar ratios:
        from 40 to 60% of leucine in molecular weight;
        from 20 to 40% of isoleucine in molecular weight;
        from 20 to 40% of valine in molecular weight,
    wherein the sum of the amounts of leucine, isoleucine and valine being between 30 to 60% of the sum in molecular weight of all the active ingredients,
    wherein the stoichiometric ratio of leucine, isoleucine and valine is 2:1:1,
    wherein the ratio between cyst(e)ine and methionine is 50 to 200% greater for cyst(e)ine on a w/w molar ration, and
    wherein tryptophan is up to 10% of the weight of all other amino acids, on a molar weight basis.

* * * * *

UNITED STATES PATENT AND TRADEMARK OFFICE
CERTIFICATE OF CORRECTION

| | |
|---|---|
| PATENT NO. | : 8,536,216 B2 |
| APPLICATION NO. | : 13/014294 |
| DATED | : September 17, 2013 |
| INVENTOR(S) | : Francesco Saverio Dioguardi |

It is certified that error appears in the above-identified patent and that said Letters Patent is hereby corrected as shown below:

1. On the Title Page, Item (54) and in the Specification, Column 1, line 1, Title, please delete "COMPOSITIONS BASED ON AMINO ACIDS" and insert --COMPOSITIONS BASED ON AMINO ACIDS, SUITABLE FOR THE TREATMENT OF HEAR FAILURE--

2. On the Title Page, Item (73) Assignee, please delete "Professional Dietetics S.R.L." and insert --Determinants of Metabolism Research Laboratory S.r.l.--

Signed and Sealed this
Eighth Day of April, 2014

Michelle K. Lee
*Deputy Director of the United States Patent and Trademark Office*